(12) United States Patent
Kleyman

(10) Patent No.: US 9,421,032 B2
(45) Date of Patent: Aug. 23, 2016

(54) SEAL PORT WITH BLOOD COLLECTOR

(75) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 416 days.

(21) Appl. No.: 13/031,352

(22) Filed: Feb. 21, 2011

(65) Prior Publication Data

US 2011/0313250 A1    Dec. 22, 2011

Related U.S. Application Data

(60) Provisional application No. 61/355,379, filed on Jun. 16, 2010.

(51) Int. Cl.
*A61B 1/32* (2006.01)
*A61B 17/34* (2006.01)

(52) U.S. Cl.
CPC ..... *A61B 17/3423* (2013.01); *A61B 2017/3419* (2013.01); *A61B 2017/3429* (2013.01); *A61B 2017/3437* (2013.01); *A61B 2017/3445* (2013.01); *A61B 2017/3464* (2013.01); *A61B 2017/3466* (2013.01)

(58) Field of Classification Search
CPC ............... A61B 17/02; A61B 17/0206; A61B 17/0218; A61B 17/0231; A61B 17/025; A61B 17/0281; A61B 17/0293
USPC ........ 600/201–249, 573, 579; 604/35, 39, 40, 604/43, 164.01, 164.02, 506, 175; 606/185, 606/167, 170, 184
See application file for complete search history.

(56) References Cited

U.S. PATENT DOCUMENTS

| | | | |
|---|---|---|---|
| 5,159,921 A | 11/1992 | Hoover | |
| 5,437,683 A | 8/1995 | Neumann et al. | |
| 5,514,153 A | 5/1996 | Bonutti | |
| 5,842,971 A | 12/1998 | Yoon | |
| 6,018,094 A | 1/2000 | Fox | |
| 6,033,426 A | 3/2000 | Kaji | |
| 6,086,603 A | 7/2000 | Termin et al. | |
| 6,440,061 B1 | 8/2002 | Wenner et al. | |
| 6,454,783 B1 | 9/2002 | Piskun | |
| 7,033,319 B2 * | 4/2006 | Pulford et al. | 600/208 |
| 7,344,547 B2 * | 3/2008 | Piskun | 606/185 |
| 7,798,898 B2 | 9/2010 | Luciano, Jr. et al. | |
| 7,837,612 B2 | 11/2010 | Gill et al. | |

(Continued)

FOREIGN PATENT DOCUMENTS

| | | |
|---|---|---|
| EP | 1 774 918 A1 | 4/2007 |
| EP | 2 044 889 A1 | 4/2009 |

(Continued)

OTHER PUBLICATIONS

U.S. Appl. No. 12/961,560, filed Dec. 7, 2010, David Farascioni.

(Continued)

*Primary Examiner* — Eduardo C Robert
*Assistant Examiner* — Michelle C Eckman

(57) ABSTRACT

An access assembly for insertion through a single incision is provided. The access assembly includes a foam body having a proximal end and a distal end and a plurality of lumens extending through the foam body. Each of the lumens includes a sleeve extending the length of the body. The foam body has a central portion and a lower rim at a distal end of the central portion. The lower rim defines a circular recess, about the body, along a proximal side of the lower rim.

15 Claims, 5 Drawing Sheets

(56) References Cited

U.S. PATENT DOCUMENTS

| | | | |
|---|---|---|---|
| 8,262,568 B2* | 9/2012 | Albrecht et al. | 600/206 |
| 2004/0260153 A1* | 12/2004 | Pulford et al. | 600/208 |
| 2006/0212063 A1 | 9/2006 | Wilk | |
| 2006/0247499 A1 | 11/2006 | Butler et al. | |
| 2006/0247500 A1* | 11/2006 | Voegele et al. | 600/208 |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh, II et al. | |
| 2006/0270911 A1 | 11/2006 | Voegele et al. | |
| 2008/0255519 A1 | 10/2008 | Piskun et al. | |
| 2009/0012477 A1 | 1/2009 | Norton et al. | |
| 2009/0093752 A1* | 4/2009 | Richard | A61B 17/3423 604/24 |
| 2009/0187079 A1* | 7/2009 | Albrecht et al. | 600/206 |
| 2009/0204067 A1 | 8/2009 | Abu-Halawa | |
| 2009/0306629 A1* | 12/2009 | Kucklick | A61B 1/015 604/541 |
| 2009/0326332 A1 | 12/2009 | Carter | |
| 2010/0030032 A1* | 2/2010 | Voegele et al. | 600/210 |
| 2010/0041957 A1* | 2/2010 | Urano et al. | 600/236 |
| 2010/1006345 | 3/2010 | Edelman et al. | |
| 2010/0094227 A1 | 4/2010 | Albrecht et al. | |
| 2010/0174149 A1* | 7/2010 | Moll et al. | 600/203 |
| 2010/0249523 A1* | 9/2010 | Spiegal et al. | 600/206 |
| 2010/0298646 A1* | 11/2010 | Stellon | A61B 17/3423 600/208 |
| 2011/0054257 A1* | 3/2011 | Stopek | 600/206 |
| 2011/0082343 A1* | 4/2011 | Okoniewski | 600/208 |
| 2011/0124970 A1* | 5/2011 | Kleyman | 600/208 |
| 2011/0196302 A1* | 8/2011 | Gildersleeve et al. | 604/151 |
| 2011/0251465 A1* | 10/2011 | Kleyman | 600/208 |
| 2011/0306842 A9* | 12/2011 | Voegele et al. | 600/206 |
| 2012/0083660 A1* | 4/2012 | Okoniewski | 600/207 |
| 2012/0130179 A1* | 5/2012 | Rockrohr | 600/205 |
| 2012/0130181 A1* | 5/2012 | Davis | 600/206 |
| 2012/0130185 A1* | 5/2012 | Pribanic | 600/208 |
| 2012/0130187 A1* | 5/2012 | Okoniewski | 600/208 |
| 2012/0209077 A1* | 8/2012 | Racenet | 600/206 |
| 2012/0245423 A1* | 9/2012 | Rodrigues | 600/205 |
| 2012/0253136 A1* | 10/2012 | Rodrigues, Jr. | 600/208 |

FOREIGN PATENT DOCUMENTS

| | | |
|---|---|---|
| EP | 2 080 494 A1 | 7/2009 |
| WO | WO 97/33520 | 9/1997 |
| WO | WO2006/110733 A2 | 10/2006 |
| WO | WO2008/015566 A2 | 2/2008 |
| WO | WO2008/121294 A1 | 10/2008 |

OTHER PUBLICATIONS

U.S. Appl. No. 13/091,246, filed Apr. 21, 2011, Paul D. Richard.
U.S. Appl. No. 13/030,164, filed Feb. 18, 2011, Gennady Kleyman.
U.S. Appl. No. 13/030,172, filed Feb. 18, 2011, Gennady Kleyman.
U.S. Appl. No. 13/030,178, filed Feb. 18, 2011, Gennady Kleyman.
U.S. Appl. No. 13/031,346, filed Feb. 21, 2011, Gennady Kleyman.
U.S. Appl. No. 13/031,352, filed Feb. 21, 2011, Gennady Kleyman.
European Search Report EP08253236 dated Feb. 10, 2009.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report dated Jul. 1, 2013 from corresponding European Patent Application No. 11250591.2. (6 pgs.).

* cited by examiner

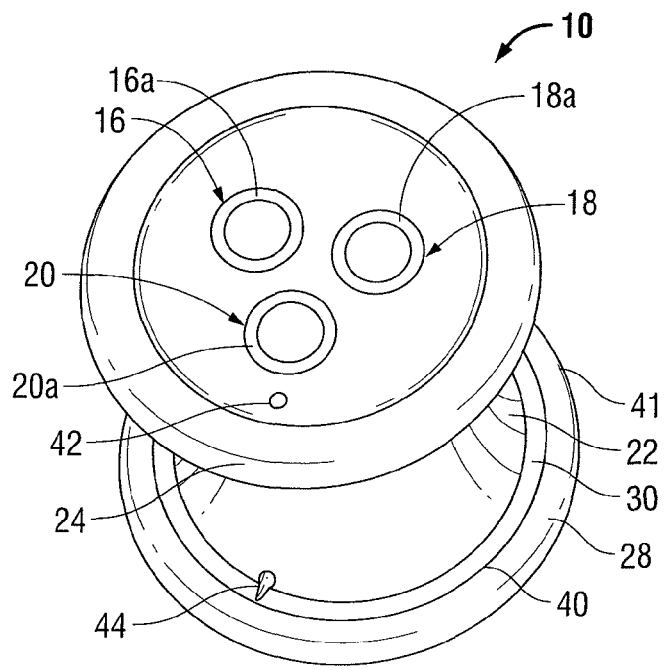
FIG. 1
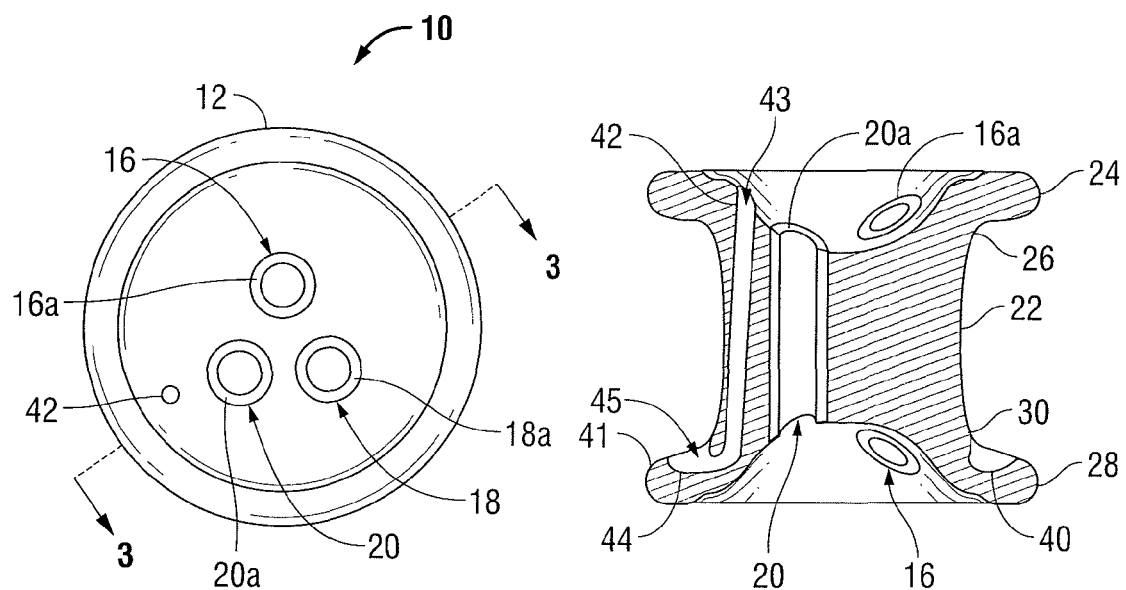
FIG. 2
FIG. 3

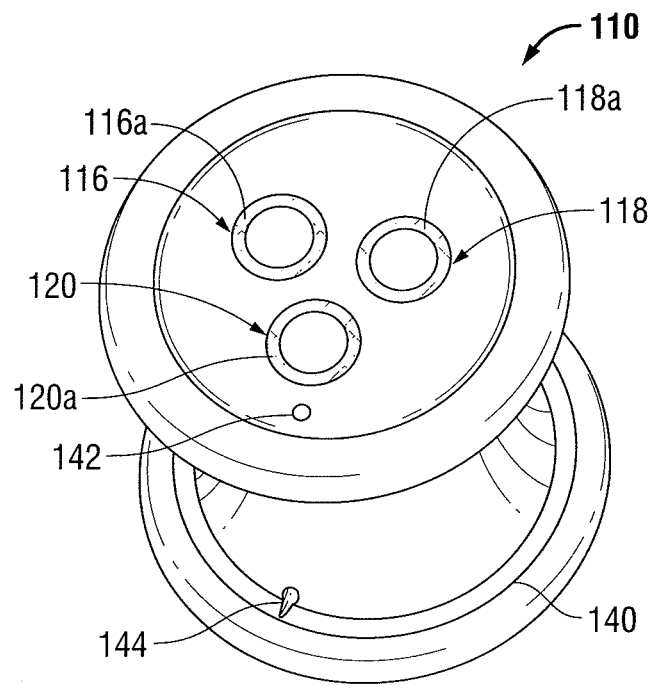
FIG. 8
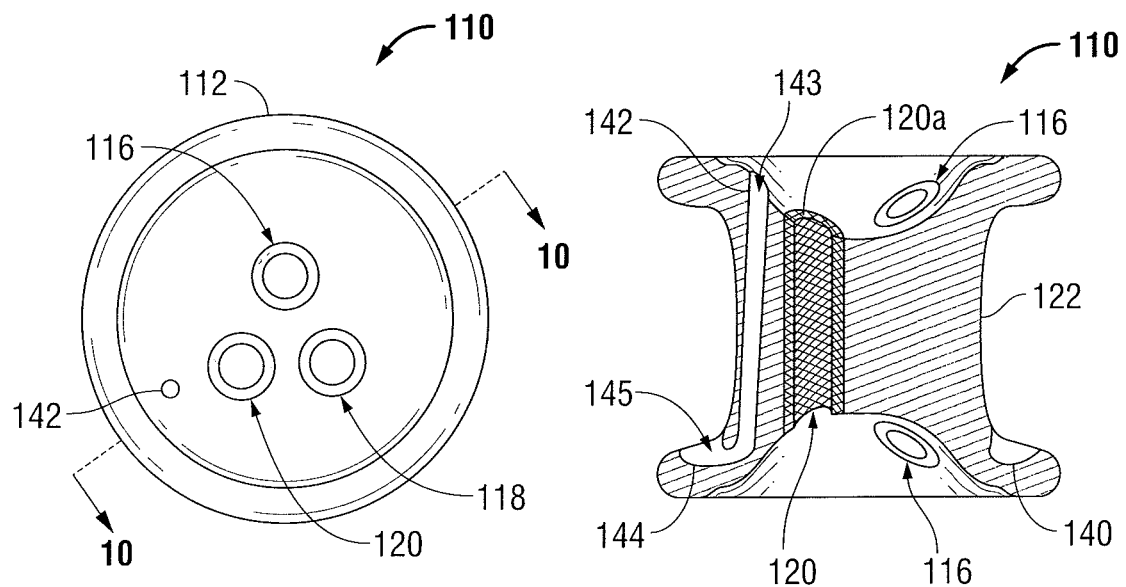
FIG. 9
FIG. 10

SEAL PORT WITH BLOOD COLLECTOR

CROSS REFERENCE TO RELATED APPLICATION

The present application claims the benefit of and priority to U.S. Provisional Application Ser. No. 61/355,379 filed on Jun. 16, 2010, the entire contents of which are incorporated herein by reference.

BACKGROUND

1. Technical Field

The present disclosure relates to a flexible access assembly for use in single incision surgical procedures. More particularly, the present disclosure relates to a flexible access assembly having a mechanism for the removal of bodily fluids.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through the incision in tissue. In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various access devices with valves and seals are used during the course of minimally invasive procedures and are widely known in the art. However, a continuing need exists for surgical access devices that can facilitate the accessibility of an underlying tissue site with relative ease and with minor inconvenience for the surgeon.

SUMMARY

Accordingly, an access assembly for insertion through a single incision is disclosed herein. The access assembly includes a body, e.g., a foam body, having a proximal end and a distal end and a plurality of lumens extending through the foam body, each of the lumens including a sleeve extending at least a portion of the length of the body. The foam body includes a central portion and a lower rim at a distal end of the central portion. The lower rim defines a circular recess, about the body, along a proximal side of the lower rim.

The body has an upper rim at a proximal end of the central portion. Both the lower rim and an upper rim have a diameter greater than a diameter of the central portion. The access assembly may define four lumens. The sleeves are integrally formed with the body, or instead, the sleeves may be securely affixed with the body. The sleeves may be formed from one polymer and plastic. The sleeves may define a circular cross-section. The sleeves may include a braided material. The access assembly may further include one or more cannula assemblies inserted through the plurality of lumens. The body may include a Parylene coating. Various other coatings, e.g., hydrophilic, hydrophobic, bio-agents, anti-infection, analgesic, may also be employed.

DESCRIPTION OF THE DRAWINGS

Various embodiments of the present disclosure are described hereinbelow with reference to the drawings, wherein:

FIG. 1 is a perspective view of an embodiment of an access assembly according to the present disclosure;

FIG. 2 is a top view of the access assembly of FIG. 1;

FIG. 3 is a cross-sectional side view of the access assembly of FIGS. 1 and 2 taken along line 3-3 of FIG. 2;

FIG. 8 is a perspective view of an alternative embodiment of an access assembly according to the present disclosure;

FIG. 9 is a top view of the access assembly of FIG. 10; and

FIG. 10 is a cross-sectional side view of the access assembly of FIGS. 9 and 10 taken along line 10-10 of FIG. 9.

Figure 4:
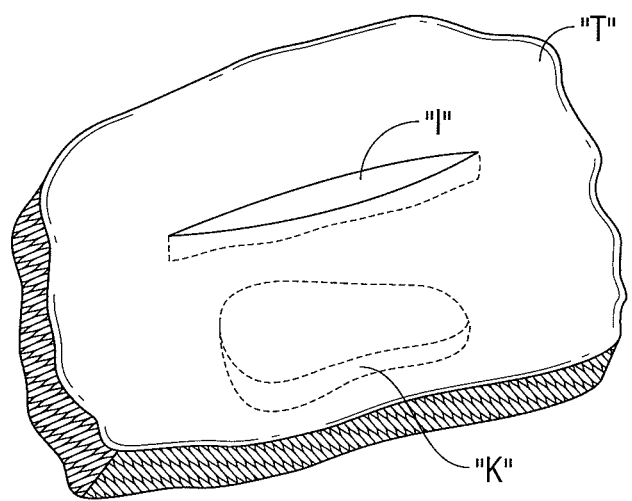
FIG. 4 is a perspective view of a tissue section having an incision therethrough with an underlying body organ shown in phantom.

Other features of the present disclosure will become apparent from the following detailed description, taken in conjunction with the accompanying drawings, which illustrate, by way of example, the principles of the present disclosure.

DETAILED DESCRIPTION

Embodiments of the presently disclosed access assembly will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

One type of minimal invasive surgery described herein is multiple instrument access through a single surgical port. This technique is a minimally invasive surgical procedure, which permits a surgeon to operate through a single entry point, typically the patient's navel. The disclosed procedure involves insufflating the body cavity with a housing member positioned within an opening in the patient's skin. Instruments including an endoscope and additional instruments such as graspers, staplers, forceps or the like may be introduced within the port to carry out the surgical procedure. The presently disclosed access port may be used with a surgically created incision, a naturally occurring opening such as the anus or the vagina, or in non-laparoscopic procedures.

Referring to FIGS. 1-3, there is disclosed an access assembly 10 for use in single incision surgery. Access assembly 10 is flexible or compressible to allow it to be inserted through a single incision in the body of a patient such that after insertion it will expand and seal within the incision. Additionally, the flexible nature of access assembly 10 allows surgical instruments inserted therethrough to be manipulated about their axes and thus allow a higher degree of movement of the surgical instruments to orient them relative to the tissue being operated upon.

Still referring to FIGS. 1-3, access assembly 10 includes a flexible body or housing 12 defining a plurality of lumens 16, 18, 20. Body 12 may be formed of various materials such as, for example, silicone, thermoplastic elastomers (TPE), rubber, foam, gel, etc. In this manner, body 12 of access assembly 10 may be compressed or squeezed and inserted through an incision in the body of a patient. In one embodiment, body 12 includes TPE material that is infused with an inert gas, e.g. $CO_2$ or nitrogen, to form a foam structure. Body 12 may be coated with a lubricant, e.g. Parylene N or C, in order to create a lubricious surface finish on all external surfaces. Various other coatings, e.g., hydrophilic, hydrophobic, bio-agents, anti-infection, analgesic, may also be employed. In this manner, the coating facilitates insertion of body 12 into an incision and insertion of cannula assemblies (FIG. 7) therethrough.

With reference still to FIGS. 1-3, body 12 defines a substantially hourglass shape when viewed from the side, including a central portion 22 having an upper rim 24 located at a proximal end 26 of central portion 22 and a lower rim 28 located at a distal end 30 of central portion 22. Upper rim 24 and lower rim 28 aid in preventing movement of access assembly 10 longitudinally through the incision "I" (FIG. 4) in the patient. The lower rim 28 defines a circular recess 40 along a proximal side 41 of the lower rim 28. The recess 40 encircles the body 12 to form a circular indentation completely about the body 12.

A vertical lumen 42 extends through the body 12 and connects with a horizontal lumen 44 to produce a longitudinal passageway 43 that extends from the proximal end 26 of the central portion 22 to a horizontal passageway 45 that extends into the recess 40. It is contemplated that passageway 43 and/or passageway 45 may be coated with an anti-coagulant.

As disclosed, the recess 40 is defined by a semi-circular cross-section. However, it is contemplated that any cross-sectional shape may be used. It is also contemplated that the horizontal lumen 44 may intersect with the recess 40 from any relative position, including along a bottom of the recess 40. It is further contemplated that the cross-sectional shape may vary about a circumference of the recess 40.

Lumens 16, 18, 20 extend through body 12 and define longitudinal axes configured to receive a cannula assembly 50 (FIG. 7), a valve assembly 60 and/or other insufflation apparatus. As shown, lumens 16, 18, 20 include sleeves 16a, 18a, 20a, respectively, extending the length of body 12. Sleeves 16a, 18a, 20a may be integrally formed with body 12, or instead may be securely affixed to body 12 using adhesive, ultrasonic welding or other suitable means. Sleeves 16a, 18a, 20a are formed of a plastic, polymer or other suitable material and are configured to prevent tearing of body 12 as a cannula assembly or other apparatus is inserted therethrough. Sleeves 16a, 18a, 20a are typically foamed of a harder or less flexible material than body 12 to resist stretching. Sleeves 16a, 18a, 20a may also be coated with a lubricant to assist in insertion of cannula assemblies 50 and/or valve assembly 60.

Referring now to FIGS. 4-7, the use of access assembly 10 in a single incision surgical procedure will now be described. Although access assembly 10 will be described as relates to relates to a procedure for excising and removing a body organ, the aspects of the present disclosure may be modified for use in any closed procedure and should not be read as limited to the procedure herein described.

Figure 5:
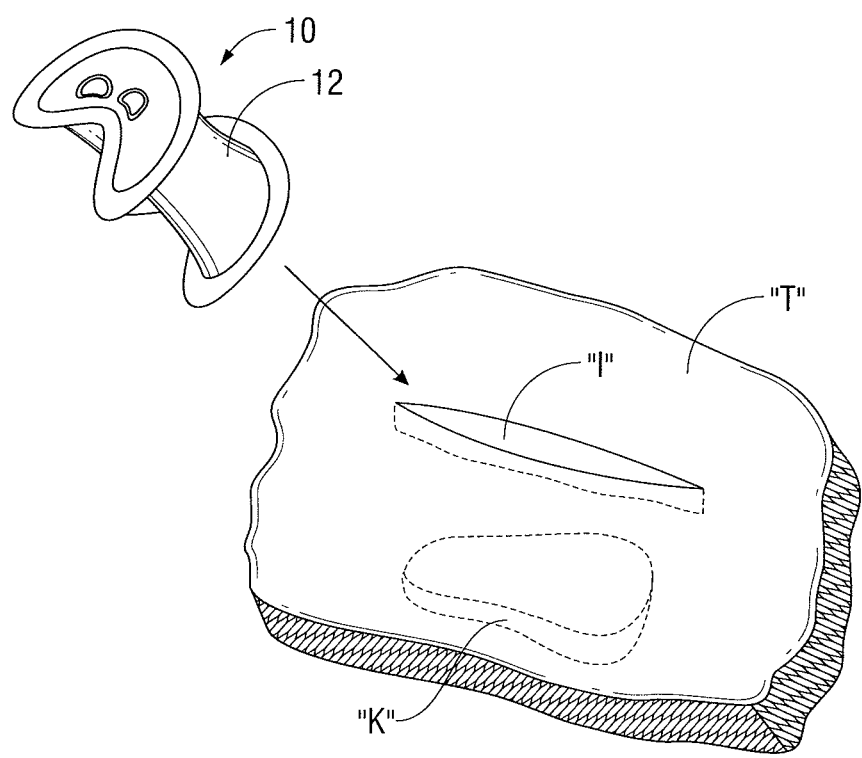
FIG. 5 is a perspective view of the access assembly of FIG. 1 prepared for insertion through the incision in the tissue.

Referring initially to FIG. 4, a single incision "I" is formed through a body tissue "T" and above a body organ, such as, for example, kidney "K". Turning now to FIG. 5, once incision "I" has been formed through body tissue "T", body 12 of access assembly 10 is squeezed or compressed to reduce body 12 to a relatively smaller diameter for insertion through incision "I". As noted hereinabove, body 12 is formed of a flexible material which allows access assembly 10 to be compressed. It should be recognized that the body 12 may be compressed into any suitable configuration prior to being inserted into an incision, not merely the configuration shown in FIG. 5. For example, in an embodiment, prior to insertion the body 12 is clamped at its distal end while the proximal end of the housing 12 remains essentially uncompressed, and the clamped distal end is inserted into the incision.

Figure 6:
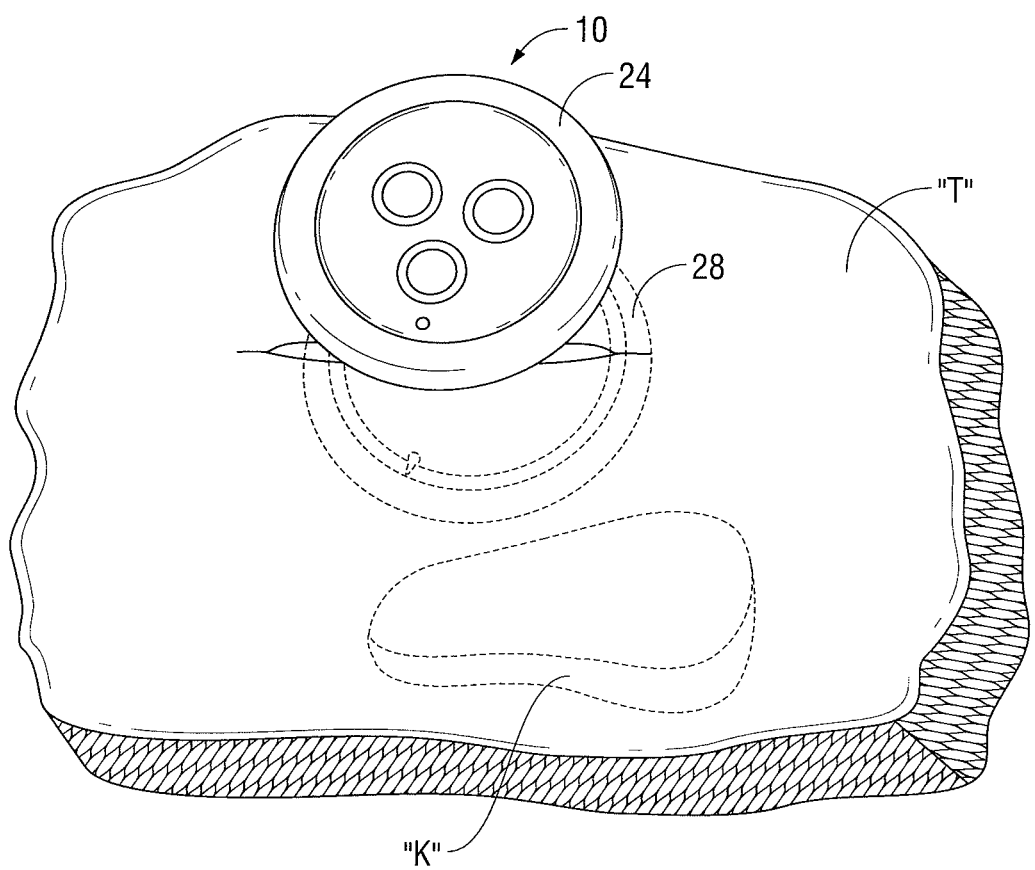
FIG. 6 is a perspective view of the flexible access assembly of FIG. 1 positioned through the incision in the tissue.

Referring to FIG. 6, once flexible access assembly 10 has been inserted through incision "I", pressure on body 12 is released, allowing body 12 to return towards its initial uncompressed state within incision "I". Typically, the incision "I" is formed having a size that is smaller than the diameter of the initial uncompressed state of the housing 12. In this manner, when in place within the incision "I", the housing 12 contacts and presses against the inner surface of the incision "I", thereby retracting the opening and sealing with the incision "I". Since incisions are often slit-shaped when formed, the portion of the housing 12 that is located within the incision may be somewhat oval-shaped (when viewed from above). As noted hereinabove, body 12 includes upper rim 24 and lower rim 28 to prevent migration of access assembly 10 through incision "I" in body tissue "T".

Figure 7:
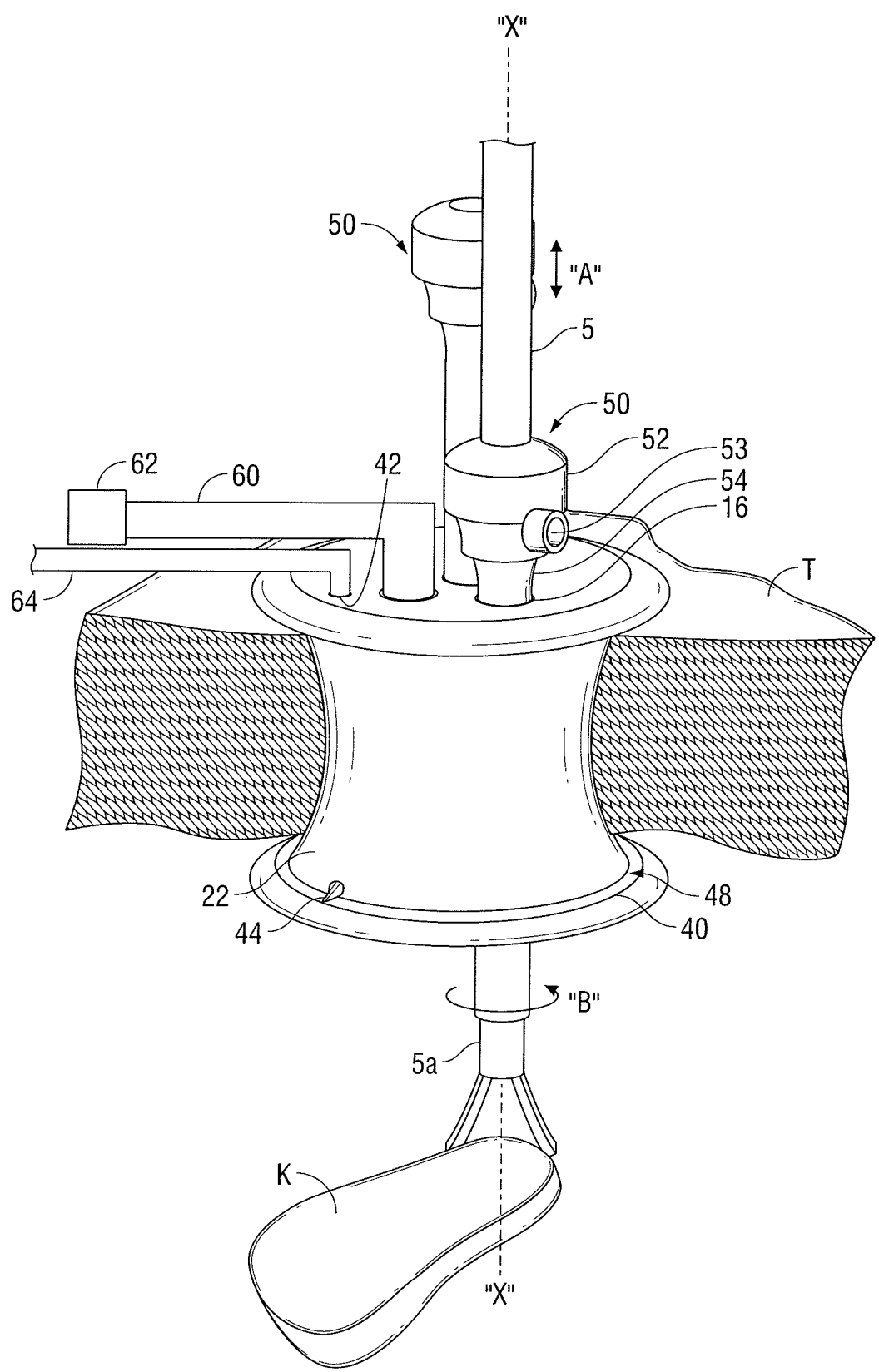
FIG. 7 is a side view, partially shown in cross-section, of the access assembly of FIG. 1, including a stopcock valve and a pair of cannula assemblies received therethrough.

Turning to FIG. 7, once access assembly 10 has been positioned above kidney "K", cannula assemblies 50 and/or valve assembly 60 may be inserted through seal lumens 16, 18, 20 to operate on kidney "K". Cannula assembly 50 includes a housing 52 configured to sealingly receive an instrument 5 and an elongated cannula 52 configured to extend through one of lumens 16, 18, 20. Housing 52 may include an insufflation port 53. Although shown including cannula assembly 50, any cannula assembly capable of being received through lumens 16, 18, 20 may be used with access assembly 10. Valve assembly 60 is configured to be received through one of lumens 16, 18, 20. Valve assembly 60 may include a stopcock or other type of valve 62 for selectively providing insufflation gas through access assembly 10. Although shown including valve assembly 60, any valve assembly capable of sealed reception within lumens 16, 18, 20 may be used with access assembly 10.

Still referring to FIG. 7, once the body cavity has been properly insufflated, either through valve assembly 60 or insufflation port 53 of cannula assembly 50, kidney "K" may be operated upon to excise it from the surrounding tissue. One or more surgical instruments, such as, for example, tissue graspers or surgical staplers, are inserted through and manipulated within cannula assemblies 50 to complete the procedure. As shown, instrument 5 may be inserted and retracted, in the direction of arrows "A", through any of seal lumens 16, 18, 20 that have received a cannula assembly 50 therethrough. Due to the flexible nature of access assembly 10, cannula assembly 50 may be flexed relative thereto. In this manner, once instrument 5 is inserted through cannula assembly 50, a proximal end 5a of instrument 5 may be manipulated in any direction, as indicated by arrows "B". Thus, access assembly 10 permits a surgeon to manipulate or orient instrument 5 at various locations relative to the tissue being operated upon. Cannula assemblies 50 may also be flexed relative to each other. In this manner, a first instrument inserted through a first cannula assembly may be manipulated relative to a second instrument inserted through a second cannula assembly.

With continued reference to FIG. 7, the recess 40 functions to collect bodily fluids 48 from the incision "I". A vacuum source 64 may be connected with the vertical lumen 42, which is connected with the recess 40 by the horizontal lumen 44. As a result, any bodily fluids 48 that are collected within the recess 40 can be removed. Thus, bodily fluids 48 may be collected and dispensed with during a minimally invasive surgical procedure to aid in the prevention of contamination and visual impairment of the surgical work site.

Upon completion of the procedure, cannula assemblies 50 and valve assembly 60 are removed from respective lumens 16, 18, 20. Access assembly 10 is then compressed or squeezed such that it may be removed from incision "I". Incision "I" is then closed in a conventional manner.

Turning now to FIGS. 4-6, an alternative embodiment of an access assembly according to the present disclosure is shown generally as access assembly 110. Access assembly 110 is substantially similar to access assembly 10 described hereinabove, and will only be described as relates to the differences therebetween. Access assembly 110 includes a body 112 defining a plurality of lumens 116, 118, 120. Each of lumens 116, 118, 120 includes a sleeve 116a, 118a, 120a, respectively. Each of sleeves 116a, 118a, 120a is formed of a braided mesh. As with sleeves 16a, 18a, 20a, described hereinabove, sleeves 116a, 118a, 120a are configured to prevent tearing of body 112 as cannula assembly and other apparatus are inserted therethrough.

It will be understood that various modifications may be made to the embodiments disclosed herein. For example, as noted hereinabove, the disclosed flexible access assembly may be provided with multiple lumens in excess of the disclosed three lumens. Additionally, the diameters or configuration of the disclosed lumens need not be identical but may be varied depending upon the contemplated surgical instruments to be utilized therethrough. Therefore, the above description should not be construed as limiting, but merely as exemplifications of particular embodiments. Those skilled in the art will envision other modifications within the scope and spirit of the claims appended hereto.

The invention claimed is:

1. An access assembly for insertion through tissue, the access assembly comprising:
    a foam body having a proximal end, a distal end, a central portion, and a lower rim extending radially outward from a distal end of the central portion, the lower rim defining an annular groove extending distally from a proximal side of the lower rim;
    a plurality of lumens extending through the foam body, each of the plurality of lumens including a sleeve extending through at least a portion of the foam body; and
    a fluid lumen extending between the proximal end and the lower rim of the foam body, the fluid lumen including an opening on the proximal side of the lower rim and in fluid communication with the annular groove, the fluid lumen configured for the extraction of the bodily fluids from the annular groove.

2. The access assembly as recited in claim 1, wherein the foam body has an upper rim at a proximal end of the central portion.

3. The access assembly as recited in claim 2, wherein the upper rim has a diameter greater than a diameter of the central portion.

4. The access assembly as recited in claim 1, wherein the plurality of lumens includes three lumens.

5. The access assembly as recited in claim 1, wherein the sleeves are integrally formed with the foam body.

6. The access assembly as recited in claim 1, wherein the sleeves are securely affixed with the foam body.

7. The access assembly as recited in claim 1, wherein the sleeves define a circular cross-section.

8. The access assembly as recited in claim 1, further including one or more cannula assemblies inserted through the plurality of lumens.

9. The access assembly as recited in claim 1, wherein the sleeves are formed from one of polymer and plastic.

10. The access assembly as recited in claim 1, wherein the foam body includes a coating that is at least one of parylene, hydrophilic, hydrophobic, bio-agents, anti-infection or analgesic.

11. The access assembly as recited in claim 1, wherein the fluid lumen is coupled to a vacuum source.

12. The access assembly as recited in claim 1, wherein the fluid lumen includes a longitudinal passageway extending from the proximal end of the central portion to a horizontal passageway, the horizontal passageway extending from the longitudinal passageway into the lower rim of the foam body, the horizontal passageway being in fluid communication with the opening of the fluid lumen.

13. The access assembly as recited in claim 12, wherein the horizontal passageway is substantially perpendicular to the longitudinal passageway.

14. An access assembly for insertion through tissue, the access assembly comprising:
    a foam body having a proximal end, a distal end, a central portion extending between the proximal end and the distal end, and a lower rim extending radially outward from a distal end of the central portion, the lower rim defining a circular groove extending distally from a proximal side of the lower rim;
    a fluid lumen extending between the proximal end and the lower rim of the foam body, the fluid lumen including an opening on the proximal side of the lower rim and in fluid communication with the circular groove, the fluid lumen configured for the extraction of the fluids from the circular groove; and
    a plurality of lumens extending through the foam body, each of the plurality of lumens including a sleeve extending through at least a portion of the foam body.

15. An access assembly for insertion through tissue, the access assembly comprising:
    a foam body having a proximal end, a distal end, a central portion, and a lower rim at a distal end of the central portion, the lower rim extending radially outward from the central portion, the lower rim defining an annular groove extending distally from a proximal side of the lower rim, the annular groove configured to collect bodily fluids;
    a plurality of lumens extending through the foam body; and
    a fluid lumen extending between the proximal end and the lower rim of the foam body, the fluid lumen including an opening on the proximal side of the lower rim and in fluid communication with the annular groove, the fluid lumen configured for the extraction of the bodily fluids from the annular groove.

* * * * *